US008026479B2

(12) United States Patent  
Lock et al.

(10) Patent No.: US 8,026,479 B2
(45) Date of Patent: Sep. 27, 2011

(54) SYSTEMS AND METHODS FOR ANALYZING SUBSTANCES USING A MASS SPECTROMETER

(75) Inventors: Chris M. Lock, Richmond Hill (CA); Nic Bloomfield, Newmarket (CA)

(73) Assignee: DH Technologies Development Pte. Ltd., Singapore (SG)

( * ) Notice: Subject to any disclaimer, the term of this patent is extended or adjusted under 35 U.S.C. 154(b) by 329 days.

(21) Appl. No.: 12/402,954

(22) Filed: Mar. 12, 2009

(65) Prior Publication Data

US 2009/0236513 A1 Sep. 24, 2009

Related U.S. Application Data

(60) Provisional application No. 61/038,068, filed on Mar. 20, 2008.

(51) Int. Cl.
*B01D 59/44* (2006.01)
(52) U.S. Cl. ........ 250/288; 250/281; 250/282; 250/287; 436/173
(58) Field of Classification Search .................. 250/281, 250/282, 287, 288, 289; 436/173
See application file for complete search history.

(56) References Cited

U.S. PATENT DOCUMENTS

| 6,107,623 | A | 8/2000 | Bateman et al. |
| 6,960,761 | B2 | 11/2005 | Clemmer |
| 7,211,791 | B2 | 5/2007 | Miller et al. |
| 7,548,818 | B2 * | 6/2009 | Kieser .............................. 702/22 |
| 2005/0277789 | A1 * | 12/2005 | Bloomfield et al. ............. 564/4 |
| 2007/0164207 | A1 * | 7/2007 | Bloomfield et al. .......... 250/282 |
| 2008/0067344 | A1 * | 3/2008 | Yamaguchi et al. .......... 250/282 |
| 2009/0014639 | A1 * | 1/2009 | Bateman ....................... 250/281 |
| 2010/0108878 | A1 * | 5/2010 | Bateman et al. .............. 250/283 |

FOREIGN PATENT DOCUMENTS

WO WO 2004012231 A2 * 2/2004

OTHER PUBLICATIONS

International Search Report and Written Opinion. Application No. PCT/CA2009/000310. Dated Jun. 29, 2009.

* cited by examiner

*Primary Examiner* — Robert Kim
*Assistant Examiner* — Michael J Logie
(74) *Attorney, Agent, or Firm* — John R. Kasha; Kasha Law LLC

(57) ABSTRACT

Systems and methods for analyzing compounds in a sample. In one embodiment, the present technology is directed towards a method of analyzing a sample, comprising: emitting ions from the sample; selectively filtering the emitted ions for at least one designated trigger ion; fragmenting the designated trigger ions; scanning for a designated trigger ion fragment; and upon detecting the designated trigger ion fragment, scanning for at least one confirmatory ion fragment.

11 Claims, 7 Drawing Sheets

| TRIGGER ION M/Z | FRAGMENT M/Z | SCANNING WINDOW | CONFIRMATORY DATA ID |
|---|---|---|---|
| 208 | 74 | 0 sec. - 15 sec. | CD10 |
| 182 | 67 | 0 sec. - 6 sec. | CD11 |
| 295 | 230 | 0 sec. - 9 sec. | CD12 |
| 153 | 76 / 92 | 142 sec. - 150 sec. | CD13 |
| 172 | 83 | 4 sec. - 12 sec. | CD14 |
| ... | ... | ... | ... |
| 213 | 60 | 0 sec. - 9 sec. | CD79 |
| 131 | 68 | 0 sec. - 13 sec. | CD80 |
| 155 | 76 | 296 sec. - 321 sec. | CD81 |

| CONFIRMATORY ID | CONFIRMATORY ION M/Z | FRAGMENT M/Z | SCANNING WINDOW DURATION |
|---|---|---|---|
| CD10 | 208 | 82 | 5 sec. |
| | 208 | 114 | |
| | 208 | 121 | |
| | 208 | 143 | |
| ... | ... | ... | ... |
| CD79 | 213 | 77 | 3 sec. |
| | 213 | 95 | |
| | 213 | 106 | |
| CD80 | 131 | 74 | 4 sec. |
| CD81 | 155 | 92 | 5 sec. |
| | 155 | 115 | |
| | 172 | 128 | |
| | 172 | 70 | |
| | 172 | 62 | |

| CONFIRMATORY ID | CONFIRMATORY ION M/Z | FRAGMENT M/Z | SCANNING DELAY |
|---|---|---|---|
| CD10 | 208 | 82 | 3 sec. |
|  | 208 | 114 |  |
|  | 208 | 121 |  |
|  | 208 | 143 |  |
| ... | ... | ... |  |
| CD79 | 213 | 77 | 1.5 sec. |
|  | 213 | 95 |  |
|  | 213 | 106 |  |
| CD80 | 131 | 74 | 2 sec. |
| CD81 | 155 | 92 | 2.5 sec. |
|  | 155 | 115 |  |
|  | 172 | 128 |  |
|  | 172 | 70 |  |
|  | 172 | 62 |  |

| PRECURSOR ION M/Z | ION FRAGMENT M/Z | SCANNING WINDOW |
|---|---|---|
| 208 | 74 | 0 sec. - 15 sec. |
| 182 | 67 | 0 sec - 6 sec. |
| 295 | 230 | 0 sec. - 9 sec. |
| 197 | 135 | 0 sec. - 17 sec. |
| ... | ... | ... |
| 199 | 148 | 0 sec. - 7 sec. |
| 202 | 78 | 0 sec. - 12 sec. |
| 213 | 60 | 0 sec. - 9 sec. |
| 131 | 68 | 0 sec. - 13 sec. |

404 — PRECURSOR ION M/Z
406 — ION FRAGMENT M/Z
408 — SCANNING WINDOW
402 — rows
402' — row with 213

| PRECURSOR ION M/Z | ION FRAGMENT M/Z | SCANNING WINDOW |
|---|---|---|
| 208 | 74 | 0 sec. - 15 sec. |
| 295 | 230 | 0 sec. - 9 sec. |
| 197 | 135 | 0 sec. - 17 sec. |
| ... | ... | ... |
| 202 | 78 | 0 sec. - 12 sec. |
| 213 | 60 | 0 sec. - 9 sec. |
| 213 | 77 | 5 sec. - 8 sec. |
| 213 | 95 | 5 sec. - 8 sec. |
| 213 | 106 | 5 sec. - 8 sec. |
| 131 | 68 | 0 sec. - 13 sec. |
| 172 | 83 | 4 sec. - 12 sec. |
| 167 | 93 | 5 sec. - 11 sec. |

Fig. 4B

SYSTEMS AND METHODS FOR ANALYZING SUBSTANCES USING A MASS SPECTROMETER

PRIORITY

The present application claims priority from U.S. provisional patent application No. 61/038,068, filed Mar. 20, 2008, which is incorporated herein by reference in its entirety.

FIELD

The present application relates generally to the field of mass spectrometry.

BACKGROUND

The analysis of a substance to determine its composition may be necessary for many applications, including toxicology, forensics and environmental testing, as well as food and drug research. Often, samples to be analyzed are analyzed for the presence of numerous different analytes of interest. Such samples may, for example, be in the form of bodily fluids taken from test subjects, which fluids often include both drug metabolites of interest, as well as irrelevant endogenous ions from the test subject. Correctly determining the presence or absence of a large number of analytes of interest from complex substances can be difficult and time-consuming.

Mass spectrometers are often used for producing a mass spectrum of a sample to find its composition. This is normally achieved by ionizing the sample and separating ions of differing masses and recording their relative abundance by measuring intensities of ion flux. For example, with time-of-flight mass spectrometers, ions are pulsed to travel a predetermined flight path. The ions are then subsequently recorded by a detector. The amount of time that the ions take to reach the detector, the "time-of-flight", may be used to calculate the ion's mass to charge ratio, m/z.

Additional information (in addition to an ion's precursor mass) can then be obtained by fragmenting the ion via CID (collision induced dissociation) in a collision cell (or other mean) to generate an MSMS spectrum. In most instruments with MSMS capabilities, the process of generating a mass spectrum, selecting a precursor ion and generating an MSMS (mass spectrum/mass spectrum) spectrum can be performed in an automated mode. This mode of acquisition is frequently referred to as Information Dependant Acquisition (IDA) or Data Dependant Experiment (DDE).

Chromatographic equipment such as a liquid chromatograph may be used to elute or release ions from a sample into the mass spectrometer over a period of time. Multiple reaction monitoring (MRM) or other distributed-analysis and recursive techniques may be used to analyze the ions received by the mass spectrometer.

Previous MRM techniques involve repeated cycles of scans by the mass spectrometer for predetermined analytes of interest. A "duty cycle" would involve a list of analytes to be "cycled through" and scanned for by the mass spectrometer. During MRM analysis, the mass spectrometer would divide its scans equally amongst the analytes of interest in the duty cycle. As a result, such duty cycles have a practical upper limit in the number of analytes which may be scanned for. Once the number of analytes grows too large (for example, some mass spectrometers require duty cycles to have no more than 50 analytes of interest in order to maintain acceptable data quality), the amount of scan time available for each analyte of interest is insufficient to provide accurate data.

The applicants have accordingly recognized a need for systems and methods for analyzing and identifying ions from samples.

SUMMARY

In one aspect, the present technology is directed towards a system for analyzing analytes in a sample. The system comprises an ion source for emitting ions from the sample; a mass spectrometer adapted to receive the ions from the ion source; a controller operatively coupled to the mass spectrometer and configured to control the first mass filter to filter for a designated ion of interest and to control the second mass filter to filter for a designated ion fragment of interest; and a trigger data set having at least one trigger entry. It should be understood that "ion fragment(s)" as used herein, are themselves ions and could alternately be referred to as "fragment ion(s)".

The mass spectrometer includes: a first mass filter to filter ions received from the ion source, an ion fragmenter configured to fragment ions received from the first mass filter, a second mass filter configured to filter ion fragments received from the ion fragmenter, and at least one detector configured to detect ion fragments received from the second mass filter. As well, each trigger entry includes: a designated trigger ion, a designated trigger ion fragment, a trigger time window, and a confirmatory data set. In turn, each confirmatory data set has at least one confirmatory entry, and each confirmatory entry includes: a designated confirmatory ion, and a designated confirmatory ion fragment. The controller is responsive to the trigger data set, and during the trigger time window for each trigger entry the controller is configured to control the first mass filter to filter for the corresponding designated trigger ion and to control the second mass filter to filter for the corresponding designated trigger ion fragment. Additionally, upon detection of the designated trigger ion fragment by the detector, the controller is configured to control the first mass filter to filter for the designated confirmatory ion and to control the second mass filter to filter for the designated confirmatory ion fragment.

The system may also include data storage operatively coupled to the controller, wherein the data storage is configured to store data corresponding to the ion fragments detected by the detector. As well, the trigger data set may comprises a plurality of trigger entries. Additionally, at least one confirmatory data set may comprise a plurality of confirmatory entries. Furthermore, the ion source may comprise a liquid chromatograph.

In another aspect, the technology is directed towards a system for analyzing ions emitted from an ion source. The system comprises: a first mass filter adapted to receive and to filter ions from the ion source, an ion fragmenter configured to fragment ions received from the first mass filter, a second mass filter configured to filter ion fragments received from the ion fragmenter, and a detector configured to detect ion fragments received from the second mass filter. The system also includes: a controller operatively coupled to the first and second mass filters, to the fragmenter and to the detector, wherein the controller is configured to control the first mass filter to filter for a designated ion of interest and to control the second mass filter to filter for a designated ion fragment of interest; a trigger data set having at least one trigger entry; and a confirmatory data set for each trigger entry. Each trigger entry includes: a designated trigger ion, a designated trigger ion fragment, and a trigger time window. Each confirmatory data set has at least one confirmatory entry, and each confirmatory entry includes: a designated confirmatory ion, and a designated confirmatory ion fragment.

The controller is responsive to the trigger data set and to the confirmatory data set, and during the trigger time window for each trigger entry the controller is configured to control the first mass filter to filter for the corresponding designated trigger ion and to control the second mass filter to filter for the corresponding designated trigger ion fragment. Upon detection of the designated trigger ion fragment by the detector, the controller is configured to control the first mass filter to filter for the designated confirmatory ion and to control the second mass filter to filter for the designated confirmatory ion fragment.

The system may also comprise data storage operatively coupled to the controller, wherein the data storage is configured to store data corresponding to the ion fragments detected by the detector. As well, the trigger data set may comprise a plurality of trigger entries. Furthermore, in some instances at least one confirmatory data set comprises a plurality of confirmatory entries.

In yet a further aspect, the present technology is directed towards a method of analyzing a sample, comprising: emitting ions from the sample; selectively filtering the emitted ions for at least one designated trigger ion; fragmenting the designated trigger ions; scanning for a designated trigger ion fragment; and upon detecting the designated trigger ion fragment, scanning for at least one confirmatory ion fragment.

The method may also include performing the filtering, fragmenting, scanning, and detecting and scanning during a trigger time window corresponding to the designated trigger ion. The trigger time window may be selected to correspond to a time period when the trigger ion is expected to be emitted from the sample.

The filtering, fragmenting, scanning, and detecting and scanning may be performed for a plurality of designated trigger ions during a plurality of trigger time windows, each trigger time window corresponding to a designated trigger ion. Each trigger time window may be selected to correspond to a time period when the corresponding trigger ion is expected to be emitted from the sample. In some instances, the scanning may be performed substantially simultaneously for at least two different designated trigger ion fragments.

The method may further comprise generating a report containing data corresponding to the detected designated trigger ion fragments and confirmatory ion fragments.

In some instances, the method may involve using liquid chromatography for emitting ions.

In another aspect, the invention may be directed to computer readable media configured to cause a mass spectrometer having a computer controller to perform the method.

BRIEF DESCRIPTION OF THE DRAWINGS

The present invention will now be described, by way of example only, with reference to the following drawings, in which like reference numerals refer to like parts and in which:

FIG. 2 is a is a representative example of a trigger data set as may be stored in the data storage of the mass spectrometer of FIG. 1;

FIG. 3A is a representative example of a first confirmatory data set as may be stored in the data storage of the mass spectrometer of FIG. 1;

FIG. 3B is a representative example of a second confirmatory data set as may be stored in the data storage of the mass spectrometer of FIG. 1;

FIG. 4A is a representative example of a duty cycle listing as may be stored in the data storage of the mass spectrometer of FIG. 1 at a first time during an analysis, in this example at or near the beginning of the analysis period;

FIG. 4B is a representative example of a duty cycle listing as may be stored in the data storage of the mass spectrometer of FIG. 1 at a second time during an analysis, after the duty cycles listing of FIG. 4A has been updated.

DETAILED DESCRIPTION

Figure 1:
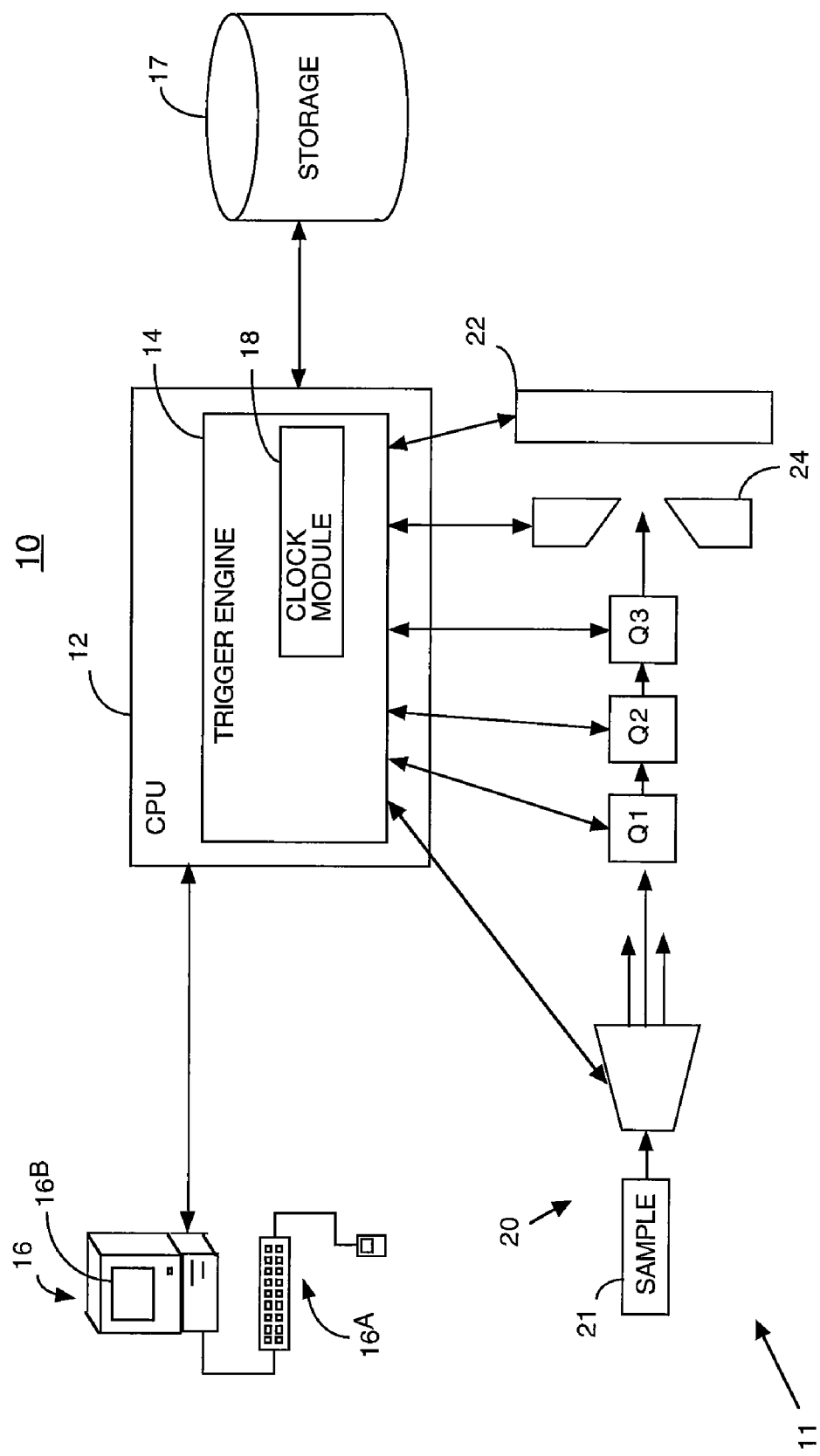
FIG. 1 is a schematic diagram of a mass spectrometer made in accordance with the present disclosure.

Referring to FIG. 1, illustrated therein is an analysis system referred to generally as 10, made in accordance with the present disclosure. The system 10 is preferably configured to be capable of performing information dependent acquisition (IDA) in accordance with the present disclosure, as will be understood.

The analysis system 10 includes a mass spectrometer 11 (which may be an MS/MS system such as a quadrupole hybrid linear ion trap such as the 4000QTRAP LC/MS/MS System sold by Applied Biosystems/MDS SCIEX). The spectrometer 11 comprises a suitably programmed controller or central processing unit (CPU) 12 having a programmed MRM trigger engine 14 stored in RAM or other suitable computer-readable media which may include a clock module 18. An input/output (I/O) device 16 (typically including an input component $16^A$ such as a keyboard or control buttons, and an output component such as a display $16^B$) is also operatively coupled to the CPU 12. Data storage 17 is also preferably provided.

The system 10 also includes an ion source 20, configured to emit ions, generated from the sample 21 to be analyzed. The ion source 20 may be a continuous ion source, for example, such as an electron impact, chemical ionization, or field ionization ion source (which may be used in conjunction with a gas chromatography source), or an electrospray or atmospheric pressure chemical ionization ion source (which may be used in conjunction with a liquid chromatography source), or a desorption electrospray ionization (DESI), or a laser desorption ionization source, as will be understood. A laser desorption ionization source, such as a matrix assisted laser desorption ionization (MALDI) can typically generate a series of pulses in which a pulsed beam of ions is emitted.

The ion source 20 can also be provided with an ion transmission ion guide, such as a multipole ion guide, ring guide, or an ion mass filter, such as a quadrupole mass filter, or an ion trapping device, as generally known in the art (not shown). For brevity, the term ion source 20 has been used to describe the components which generate ions from the sample 21, and emit analyte ions of interest for detection. Other types of ion sources 20 may also be used, such as a system having a tandem mass filter and ion trap. Preferred ion sources are those which emit the ions from the sample 21 over a range of times, to enable recursive mass analysis by the mass spectrometer 11 using MRM or other suitable techniques.

As will be understood, liquid chromatography may be used to separate ions dissolved in solvent from other substances in the sample 21, and release or emit such ions for MS analysis. As a result of the different timings for the chemical interactions that take place during the LC phase, the reaction products (which include the ions or analytes of interest) are released over time. The release times for specific analytes can be estimated, based on the expected chemical interactions.

As noted above, the spectrometer 11 may comprise a triple quadrupole mass spectrometer, having triple rod sets Q1, Q2 and Q3. The rod sets Q1 and Q3 may be controlled by the processor 12 (via the trigger engine 14) to select or filter for ions having a particular m/z. In contrast, the Q2 rod set is provided with a chamber and configured to operate as a collision cell or fragmenter for fragmenting the ions received from Q1. The resulting ion fragments may be passed through to, and selectively filtered by, rod set Q3, before being detected or recorded by the detector 22.

Optics 24 or other focusing elements, such as an electrostatic lens can also be disposed in the path of the emitted ions, typically between the Q3 rod set and the detector 22, for focusing the ions onto the detector 22.

Referring now to FIG. 2, illustrated therein is a representative example of a trigger data set 200 as may be stored in the data storage 17. The trigger data set 200 includes at least one trigger entry 202, and each trigger entry 202 includes: at least one m/z value, each such m/z value corresponding to a designated trigger ion 204, at least one m/z value, each such m/z value corresponding to a designated trigger ion fragment 206, timing data corresponding to a trigger time window 208, and linking data such as a unique identifier data 210 providing a link to a confirmatory data set 300. As will be understood, each confirmatory data set 300 need not be uniquely linked to only one designated trigger ion 204/fragment 206 couplet. In some instances, such as in the case of background noise or other interference, it may be desirable to have more than one trigger ion 204/fragment 206 couplet detected before the corresponding confirmatory data set 300 is filtered for, as will be understood.

As will also be understood, the trigger time window 208 corresponds to a predetermined period of time when the corresponding designated trigger ion 204 is expected to be emitted by the ion source 20 from the sample 21. It should also be understood that the trigger time or scanning window data 208 is not a requirement, as for certain simplified applications, the "windows" may be treated as running for the entire analysis period.

Illustrated in FIG. 3A is a representative example of a confirmatory data set 300 as may be stored in the data storage 17. Each confirmatory data set 300 has at least one confirmatory entry 302, and each confirmatory entry 302 includes: at least one m/z value, each such m/z value corresponding to a designated confirmatory ion 304, and at least one m/z value, each such m/z value corresponding to a designated confirmatory ion fragment 306. Each confirmatory entry 302 may also include timing data corresponding to a confirmatory time window 308. The example confirmatory timing window data 308 corresponds to a duration of scanning time (eg. 5 seconds). As will be understood in the context of the discussion below, in some instances, while the commencement time of an elution period may be uncertain, the duration of an elution period can often be estimated or known with greater accuracy. As a result, once the rising edge of an LC peak corresponding to the analyte of interest has been detected in accordance with the method discussed below, the system 10 may scan for the confirmatory ion(s) 304 for the duration of the expected elution period.

Each confirmatory data entry 302 also includes a unique confirmatory identifier 310, corresponding to a confirmatory data identifier 210 in the trigger data 200.

In alternate embodiments (not shown), the confirmatory time window data 308 might match the corresponding trigger time window 208 periods. In such instances the confirmatory time window data 308 need not be stored in the confirmatory data set 300, and the corresponding trigger time window 208 data may be used by the CPU 12 as required.

Illustrated in FIG. 3B, is a representative example of an alternate confirmatory data set 300B as may be stored in the data storage 17. The alternate confirmatory data set 300B generally corresponds to the confirmatory data set 300 and has at least one confirmatory entry 302, with each confirmatory entry 302 including: at least one m/z value, each such m/z value corresponding to a designated confirmatory ion 304, and at least one m/z value, each such m/z value corresponding to a designated confirmatory ion fragment 306. Each confirmatory entry 302 also includes timing data corresponding to a confirmatory time window delay 308B.

As will be understood, for certain analysis applications, such as proteomics, in which qualification data is desired (ie. a determination as to the presence of a particular analyte of interest), it may be advantageous to conduct a single scan (or limited number of scans) to confirm the presence of the confirmatory ions 304 and confirmatory ion fragments 306. For example, while a trigger ion 204 will likely be detected at the rising edge of the LC peak corresponding to the analyte of interest, the scanning for the corresponding confirmatory ion(s) 304 and fragment(s) 306 may be delayed by the confirmatory time window delay 308B to correspond to the expected LC peak apex, as will be understood.

Turning now to FIG. 4A, illustrated therein is a representative example of a duty cycle listing 400 as may be stored in the data storage 17 at a first time during an analysis, in this example, at or near the beginning of the analysis period. Each duty cycle entry 402 in the duty cycle listing 400 includes m/z data corresponding to a designated precursor ion 404, an m/z value corresponding to a designated ion fragment 406, together with a corresponding scanning window timeframe 408. Illustrated in FIG. 4B is a representative example of the duty cycle listing 400' as may be stored in the data storage 17 at a second time during an analysis, for example at about 8 seconds after the commencement of the analysis period.

As will be understood, in operation, the CPU 12/MRM trigger engine 14 is responsive to the trigger data set 200 and to the confirmatory data set 300. As will be discussed in greater detail below, the trigger engine 14 is configured to manage the duty cycle list 400 during MRM analysis, such that during the analysis period, designated precursor ion 404 and ion fragment 406 couplets 402 are added to and removed from the duty cycle list 400 over time, based on the trigger 200 and confirmatory 300 data sets, as well as the data received from the detector 22. In turn, the trigger engine 14 utilizes the ion/fragment couplets 404,406 in the duty cycle listing 400 to regulate the operation of the mass analyzers Q1 and Q3, to filter for the corresponding precursor ions 404 and confirmatory ion fragments 406.

Figure 5:
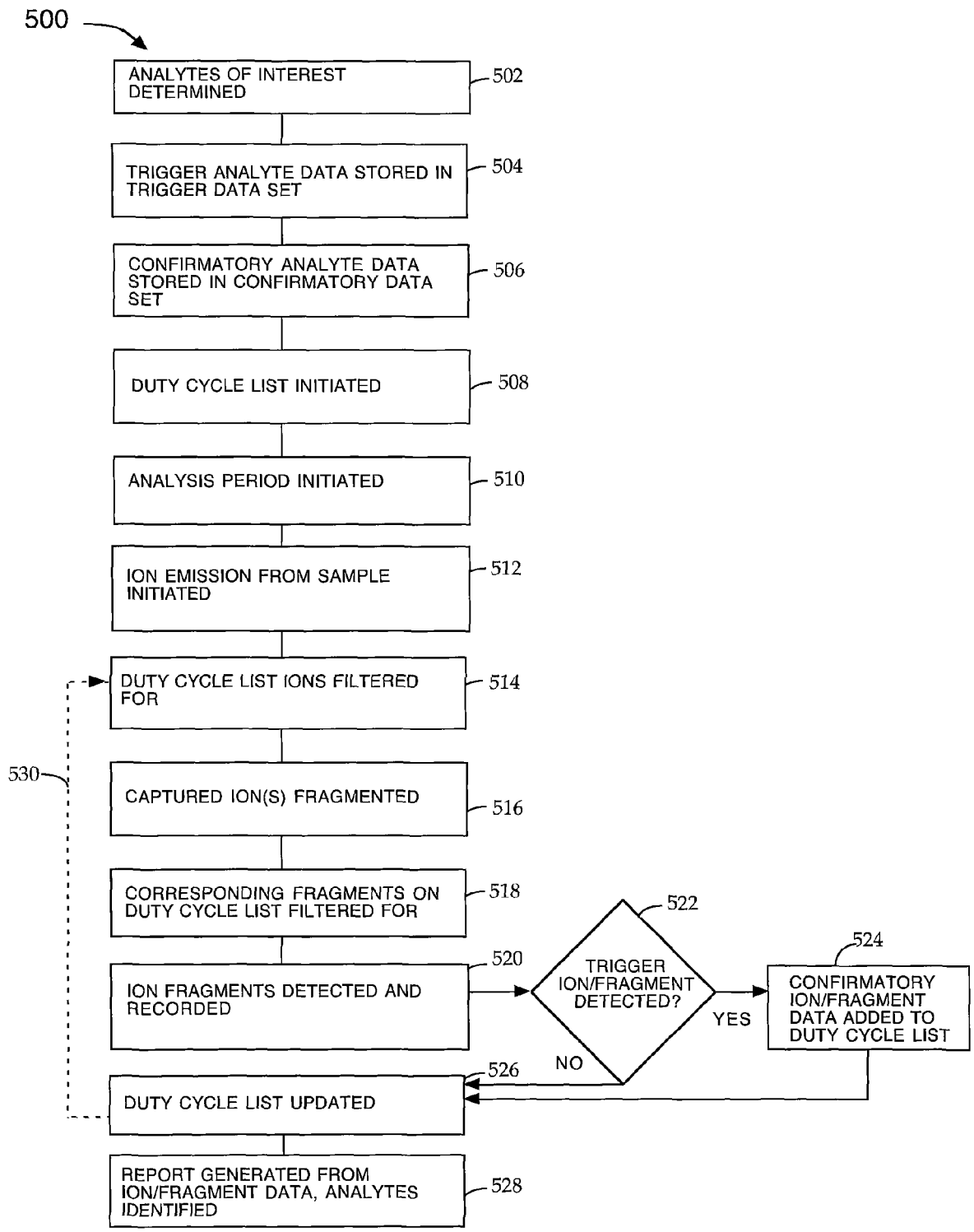
FIG. 5 is a flow diagram illustrating the steps of a method of analyzing a compound in accordance with the present disclosure.

FIG. 5 sets out the steps of the method, referred to generally as 500, carried out by the spectrometer system 10 during an analysis period. Typically, before the analysis period is commenced, the analytes of interest are determined (for which the sample is being analyzed)(Block 502). As noted above, for each analyte of interest, one or more couplets each comprising a designated precursor ion 204 and corresponding designated ion fragment 206 may be stored in a trigger entry 202 in the trigger data set 200. The corresponding trigger time window 208, is also determined and stored (Block 504).

The confirmatory data set 300 will also be determined and stored in data storage 17 (Block 506). As will be understood, typically an ion will fragment into a plurality of ion fragments. Accordingly, in many instances, the confirmatory data couplets 302 corresponding to a trigger couplet 202, will share the same precursor ion 204, 304.

As will be understood, the trigger data 200 (designated precursor ion(s) 204 and designated ion fragment(s) 206, together with the corresponding trigger time window 208) and the related confirmatory data 300 for numerous analytes of interest may be previously calculated and stored as a library of data in the data storage 17, and simply indexed and retrieved by the user and the CPU 12 utilizing the I/O device 16.

The duty cycle list 400 is initiated, being populated with couplets 402 of designated precursor ion 204 and designated ion fragment 206 from the trigger data 200 which have a trigger time window 208 which commences or coincides with the beginning of the analysis period. FIG. 4A illustrates an example duty cycle list 400 as one may exist at the commencement of an analysis period. The user will then typically input a command to commence an analysis period (typically via the I/O device 16), upon receipt of which the trigger engine 14 is programmed to initiate the analysis period (Block 510).

When the analysis period is commenced, the ion source 20 is activated to commence the emitting of ions from the sample 21 (which may be the commencement of the LC phase as outlined above)(Block 512). As will be understood, the sample compound, for example, may include bodily fluid taken from a test subject, which fluid often includes both drug metabolites of interest, as well as irrelevant endogenous ions from the test subject.

The system 10 is then configured to selectively filter the emitted ions for the designated precursor ions 404 listed on the duty cycle listing 400 (Block 514). As will be understood, at least one (if not most) of the precursor ions 404 (and designated ion fragments 406) listed on the duty cycle listing 400 corresponds to a trigger ion 204 (and trigger ion fragment 206) in the trigger data 200. As indicated by the dotted line 530, the CPU 12/trigger engine 14 is programmed to rapidly and repeatedly cycle through the designated precursor ions 404 on the duty cycle listing, and causes the rod set Q1 to selectively filter the ions received from the ion source 20 for the designated precursor ions 404.

The filtered ions 404 (which as noted, include at least one trigger ion 204), are then received by the fragmentation module/rod set Q2 and fragmented (Block 516). The fragments are then received by the Q3 rod set, which is controlled by the trigger engine 14 to scan or filter for the designated ion fragments 406 on the duty cycle listing 400 (Block 518). Such designated ion fragments 406 (if any) are permitted to impact the detector 22. As will be understood, the filtering, fragmenting and filtering steps of Blocks 514-518 are typically all performed for one ion/fragment couplet 402, prior to the trigger engine 14 cycling to the next couplet 402 on the duty cycle list 400.

If the detector 22 detects a designated trigger ion fragment 206 (Block 522), the trigger engine 14 may be programmed to cause the system 10 to scan for at least one confirmatory ion fragment. As will be understood, a certain threshold may be predetermined for "detecting" a trigger ion fragment 206—a certain quantity of trigger ion fragments 206 must be detected in order for the trigger ion fragment 206 to be considered "detected". Similarly, in the event multiple trigger ion 204/fragment 206 couplets in a trigger entry 202 must be "detected" the trigger engine 14 may be programmed to determine that such multiple trigger ion 204/fragment 206 couplets have been detected before the system 10 scans for confirmatory ion fragment(s).

The trigger engine 14 determines the confirmatory entry identifier 210 corresponding to the designated trigger ion fragment 206 (and designated trigger ion 204), and adds to the duty cycle listing 400 the one or more corresponding confirmatory couplets 302 of confirmatory ion 304 and confirmatory ion fragment 306 (linked to by the matching identifiers 210, 310) and calculates or otherwise determines the scanning window data 408 which is also added to the duty cycle listing 400 (Block 524). Referring briefly again to FIGS. 4A and 4B, the example data provides an illustrative example of the updating of a duty cycle listing 400, 400', after the designated ion 204/designated trigger ion fragment 206 couplet 202', has been detected. The designated confirmatory ion 304 and designated confirmatory ion fragment 306 data in the corresponding confirmatory entry 302' (sharing a matching confirmatory identifier 310, 210 with the detected trigger couplet 202') have been added as entries 402* to the duty cycle listing 400', together with the calculated trigger window data 408. As can be seen from the example calculated trigger window data 408* for the added entries 402*, the trigger engine 14 has detected the couplet 202' at approximately 5 seconds from the commencement of the analysis period and has calculated the trigger window data 408* as commencing at the time of detection, 5 seconds, for the duration of the corresponding scanning window duration 308 (in this case 3 seconds), to result in an entry 408* of "5 sec.-8 sec.", as will be understood.

Over time, as the time of the analysis period advances as may be tracked by the clock module 18, the duty cycle listing is updated (Block 526). As the analysis period moves into the various trigger time windows 208, the corresponding couplet 202 of designated trigger ions 204 and ion fragments 206 are added to the duty cycle listing 400. Similarly, as the time of the analysis period moves beyond the various trigger time windows 408, the corresponding couplet 402 of designated ions 404 and ion fragments 406 are removed from the duty cycle listing 400.

As will be understood, during the updating carried out in Block 526, when a trigger time window 408 has passed and the corresponding couplet 202, 402 of designated trigger ions 204, 404 and ion fragments 206, 406 are removed from the duty cycle listing 400, as well the corresponding confirmatory couplet(s) 302 of confirmatory ion(s) 304, 404 and ion fragment(s) 306, 406 are removed from the duty cycle listing 400. The process cycles through the various steps 514-526 until the analysis period is complete and ion emission is terminated.

Thus, for example, by referring to both FIGS. 4A and 4B, it is possible to compare the duty cycle listing 400 at or near the commencement of the analysis period to the duty cycle listing 400' as it may appear at approximately 7 seconds into the analysis period for the exemplary data. As can be seen, since the scanning window 408 for the ion/fragment couplet pointed to by 402''' has passed, this couplet 402''' has been removed from the duty cycle listing 400'. Similarly, as the analysis time has moved into the range of trigger or scanning windows 208, for ion/fragment couplets 202" in the trigger data set 200, such corresponding couplets 402" have been added to the duty cycle listing 400'. As will be understood, the updating step of Block 526 will be unnecessary for applications which do not involve trigger or scanning windows.

As will be understood, the controller 12 may generate a report identifying the quantities of the various designated ion/fragment couplets and hence the presence or absence of the corresponding analytes of interest (Block 528). Quantities of confirmatory couplets 302 should approximate the quantities of the corresponding trigger couplets 202, confirming both the quantity and presence of the corresponding analytes of interest, as will be understood.

Thus, while what is shown and described herein constitute preferred embodiments of the subject invention, it should be understood that various changes can be made without departing from the subject invention, the scope of which is defined in the appended claims.

The invention claimed is:

1. A system for analyzing analytes in a sample, comprising:
   (a) an ion source for emitting ions from the sample;
   (b) a mass spectrometer adapted to receive the ions from the ion source, wherein the mass spectrometer includes:
      (i) a first mass filter to filter ions received from the ion source,
      (ii) an ion fragmenter configured to fragment ions received from the first mass filter,
      (iii) a second mass filter configured to filter ion fragments received from the ion fragmenter, and
      (iv) at least one detector configured to detect ion fragments received from the second mass filter;
   (c) a controller operatively coupled to the mass spectrometer and configured to control the first mass filter to filter for a designated ion of interest and to control the second mass filter to filter for a designated ion fragment of interest;
   (d) a trigger data set having at least one trigger entry, wherein each trigger entry includes:
      (i) a designated trigger ion,
      (ii) a designated trigger ion fragment,
      (iii) a trigger time window, and
      (iv) a confirmatory data set;
   (e) wherein each confirmatory data set has at least one confirmatory entry, and wherein each confirmatory entry includes:
      (i) a designated confirmatory ion, and
      (ii) a designated confirmatory ion fragment;
   (f) wherein the controller is responsive to the trigger data set, and during the trigger time window for each trigger entry the controller is configured to control the first mass filter to filter for the corresponding designated trigger ion and to control the second mass filter to filter for the corresponding designated trigger ion fragment;
   (g) wherein upon detection of the designated trigger ion fragment by the detector, the controller is configured to control the first mass filter to filter for the designated confirmatory ion and to control the second mass filter to filter for the designated confirmatory ion fragment.

2. The system as claimed in claim 1, further comprising data storage operatively coupled to the controller, wherein the data storage is configured to store data corresponding to the ion fragments detected by the detector.

3. The system as claimed in claim 1, wherein the trigger data set comprises a plurality of trigger entries.

4. The system as claimed in claim 1, wherein at least one confirmatory data set comprises a plurality of confirmatory entries.

5. The system as claimed in claim 1, wherein the ion source comprises a liquid chromatograph.

6. The system as claimed in claim 1, wherein the ion source comprises a MALDI ionization source.

7. The system as claimed in claim 1, wherein at least one trigger entry comprises a plurality of trigger ion fragments.

8. A system for analyzing ions emitted from an ion source, the system comprising:
   (a) a first mass filter adapted to receive and to filter ions from the ion source,
   (b) an ion fragmenter configured to fragment ions received from the first mass filter,
   (c) a second mass filter configured to filter ion fragments received from the ion fragmenter, and
   (d) a detector configured to detect ion fragments received from the second mass filter;
   (e) a controller operatively coupled to the first and second mass filters, to the fragmenter and to the detector, wherein the controller is configured to control the first mass filter to filter for a designated ion of interest and to control the second mass filter to filter for a designated ion fragment of interest;
   (f) a trigger data set having at least one trigger entry, wherein each trigger entry includes:
      (i) a designated trigger ion,
      (ii) a designated trigger ion fragment, and
      (iii) a trigger time window,
   (g) a confirmatory data set for each trigger entry, wherein each confirmatory data set has at least one confirmatory entry, and wherein each confirmatory entry includes:
      (i) a designated confirmatory ion, and
      (ii) a designated confirmatory ion fragment;
   (h) wherein the controller is responsive to the trigger data set and to the confirmatory data set, and during the trigger time window for each trigger entry the controller is configured to control the first mass filter to filter for the corresponding designated trigger ion and to control the second mass filter to filter for the corresponding designated trigger ion fragment;
      (i) wherein upon detection of the designated trigger ion fragment by the detector, the controller is configured to control the first mass filter to filter for the designated confirmatory ion and to control the second mass filter to filter for the designated confirmatory ion fragment.

9. The system as claimed in claim 8, further comprising data storage operatively coupled to the controller, wherein the data storage is configured to store data corresponding to the ion fragments detected by the detector.

10. The system as claimed in claim 8, wherein the trigger data set comprises a plurality of trigger entries.

11. The system as claimed in claim 8, wherein at least one confirmatory data set comprises a plurality of confirmatory entries.

* * * * *

(12) EX PARTE REEXAMINATION CERTIFICATE (9895th)

United States Patent
Lock et al.

(10) Number: US 8,026,479 C1
(45) Certificate Issued: Oct. 22, 2013

(54) SYSTEMS AND METHODS FOR ANALYZING SUBSTANCES USING A MASS SPECTROMETER

(75) Inventors: Chris M. Lock, Richmond Hill (CA); Nic Bloomfield, Newmarket (CA)

(73) Assignee: DH Technologies Development Pte. Ltd., Singapore (SG)

Reexamination Request:
No. 90/012,730, Dec. 3, 2012

Reexamination Certificate for:
Patent No.: 8,026,479
Issued: Sep. 27, 2011
Appl. No.: 12/402,954
Filed: Mar. 12, 2009

Related U.S. Application Data

(60) Provisional application No. 61/038,068, filed on Mar. 20, 2008.

(51) Int. Cl.
*B01D 59/44* (2006.01)

(52) U.S. Cl.
USPC ........... 250/288; 250/281; 250/282; 250/287; 436/173

(58) Field of Classification Search
None
See application file for complete search history.

(56) References Cited

To view the complete listing of prior art documents cited during the proceeding for Reexamination Control Number 90/012,730, please refer to the USPTO's public Patent Application Information Retrieval (PAIR) system under the Display References tab.

*Primary Examiner* — Erik Kielin

(57) ABSTRACT

Systems and methods for analyzing compounds in a sample. In one embodiment, the present technology is directed towards a method of analyzing a sample, comprising: emitting ions from the sample; selectively filtering the emitted ions for at least one designated trigger ion; fragmenting the designated trigger ions; scanning for a designated trigger ion fragment; and upon detecting the designated trigger ion fragment, scanning for at least one confirmatory ion fragment.

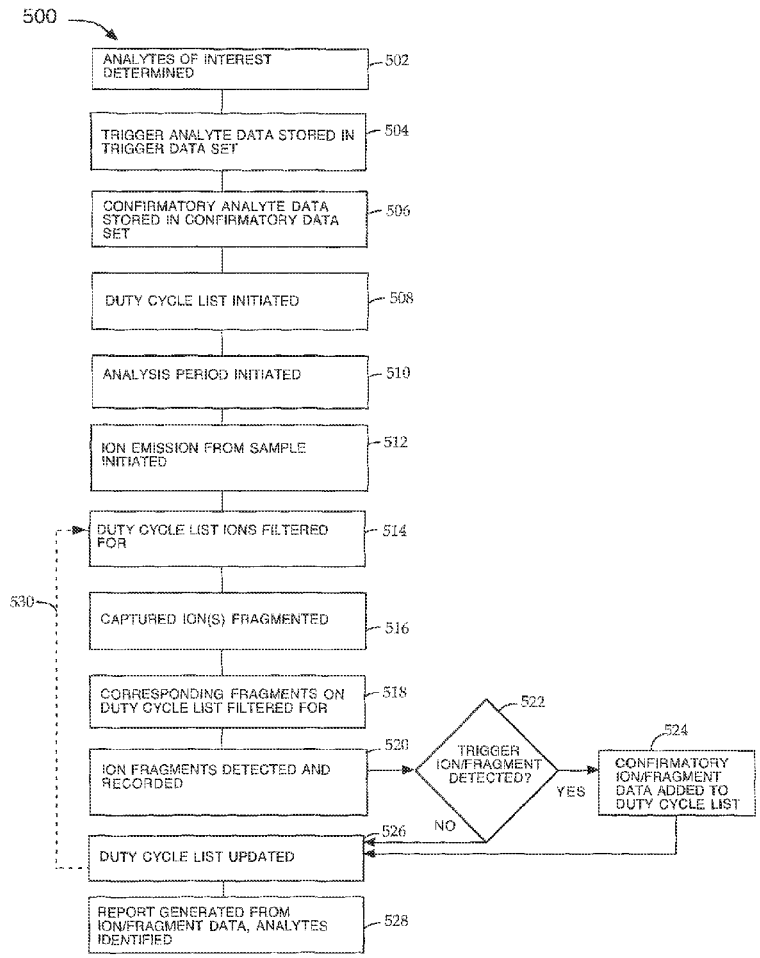

US 8,026,479 C1

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 8 are determined to be patentable as amended.

Claims 2-7 and 9-11, dependent on an amended claim, are determined to be patentable.

New claims 12-17 are added and determined to be patentable.

1. A system for analyzing analytes in a sample, comprising:
   (a) an ion source for emitting ions from the sample;
   (b) a mass spectrometer adapted to receive the ions from the ion source, wherein the mass spectrometer includes:
      (i) a first mass filter to filter ions received from the ion source,
      (ii) an ion fragmenter configured to fragment ions received from the first mass filter,
      (iii) a second mass filter configured to filter ion fragments received from the ion fragmenter, and
      (iv) at least one detector configured to detect ion fragments received from the second mass filter;
   (c) a controller operatively coupled to the mass spectrometer and configured to control the first mass filter to filter for a designated ion of interest and to control the second mass filter to filter for a designated ion fragment of interest; *and*
   (d) a trigger data set having at least one trigger entry, wherein each trigger entry includes:
      (i) a designated trigger ion,
      (ii) a designated trigger ion fragment,
      (iii) a trigger time window, and
      (iv) a confirmatory set[;],
   (e) wherein each confirmatory data set has at least one confirmatory entry, and wherein each confirmatory entry includes:
      (i) a designated confirmatory ion, and
      (ii) a designated confirmatory ion fragment[;],
   (f) wherein the controller is responsive to the trigger data set, and during the trigger time window for each trigger entry the controller is configured to control the first mass filter to filter for the corresponding designated trigger ion and to control the second mass filter to filter for the corresponding designated trigger ion fragment[;] *by selectively filtering ions emitted from the ion source for ions stored in a duty cycle list during each cycle of an analysis period and limits the number of ions on the duty cycle list for each cycle by*
      (i) *when the time of the analysis period moves into a trigger time window of a trigger data set, adding to the duty cycle list a designated trigger ion and a corresponding trigger ion fragment of the trigger data set, and*
      (ii) *when the time of the analysis period moves beyond a trigger time window of a trigger data set, removing from the duty cycle list a designated trigger ion and a corresponding trigger ion fragment of the trigger data set and, if a designated confirmatory ion and a corresponding designated confirmatory ion fragment of a confirmatory data set of the trigger data set are on the duty cycle list, removing from the duty cycle list the designated confirmatory ion and the corresponding designated confirmatory ion fragment, and*
   (g) wherein upon detection of the designated trigger ion fragment by the detector, the controller is configured to control the first mass filter to filter for the designated confirmatory ion and to control the second mass filter to filter for the designated confirmatory ion fragment *by adding to the duty cycle list a designated confirmatory ion and a corresponding designated confirmatory ion fragment of a confirmatory data set of a trigger data set of the detected designated trigger ion fragment.*

8. A system for analyzing ions emitted from an ion source, the system comprising:
   (a) a first mass filter adapted to receive and to filter ions from the ion source[,];
   b) an ion fragmenter configured to fragment ions received from the first mass filter[,];
   (c) a second mass filter configured to filter ion fragments received from the ion fragmenter [,]; *and*
   (d) a detector configured to detect ion fragments received from the second mass filter;
   (e) a controller operatively coupled to the first and second mass filters, to the fragmenter and to the detector, wherein the controller is configured to control the first mass filter to filter for a designated ion of interest and to control the second mass filter to filter for a designated ion fragment of interest;
   (f) a trigger data set having at least one trigger entry, wherein each trigger entry includes:
      (i) a designated trigger ion,
      (ii) a designated trigger ion fragment, and
      (iii) a trigger time window, *and*
   (g) a confirmatory data set for each trigger entry, wherein each confirmatory data set has at least one confirmatory entry, and wherein each confirmatory entry includes:
      (i) a designated confirmatory ion, and
      (ii) a designated confirmatory ion fragment[;],
   (h) wherein the controller is responsive to the trigger data set and to the confirmatory data set, and during the trigger time window for each trigger entry the controller is configured to control the first mass filter to filter for the corresponding designated trigger ion and to control the second mass filter to filter for the corresponding designated trigger ion fragment[;] *by selectively filtering ions emitted from the ion source for ions stored in a duty cycle list during each cycle of an analysis period and limits the number of ions on the duty cycle list for each cycle by*
      (i) *when the time of the analysis period moves into a trigger time window of a trigger data set, adding to the duty cycle list a designated trigger ion and a corresponding trigger ion fragment of the trigger data set, and*
      (ii) *when the time of the analysis period moves beyond a trigger time window of a trigger data set, removing from the duty cycle list a designated trigger ion and a corresponding trigger ion fragment of the trigger data set and, if a designated confirmatory ion and a corresponding designated confirmatory ion fragment of a confirmatory data set of the trigger data set are on* the duty cycle list, removing from the duty cycle list the designated confirmatory ion and the corresponding designated confirmatory ion fragment, and (i) wherein upon detection of the designated trigger ion fragment by the detector, the controller is configured to control the first mass filter to filter for the designated confirmatory ion and to control the second mass filter to filter for the designated confirmatory ion fragment *by adding to the duty cycle list a designated confirmatory ion and a corresponding designated confirmatory ion fragment of a confirmatory data set of a trigger data set of the detected designated trigger ion fragment.*

12. The system as claimed in claim 1, wherein each confirmatory entry further comprises timing data.

13. The system as claimed in claim 12, wherein the timing data comprises a confirmatory time window, the confirmatory time window is within and less than or equal to a trigger time window of a trigger data set that includes the each confirmatory entry, and wherein when the time of the analysis period moves beyond a confirmatory time window of the each confirmatory entry, if a designated confirmatory ion and a corresponding designated confirmatory ion fragment of the each confirmatory entry are on the duty cycle list, the controller further removes from the duty cycle list the designated confirmatory ion and the corresponding designated confirmatory ion fragment.

14. The system as claimed in claim 12, wherein the timing data comprises a confirmatory time window delay, and wherein, when a designated trigger ion fragment is detected by the detector, the controller further adds to the duty cycle list any designated confirmatory ions and corresponding designated confirmatory ion fragments from one or more stored confirmatory data sets designated by the trigger data set of the detected designated trigger ion fragment after one or more confirmatory time window delays specified by the one or more stored confirmatory data sets.

15. The system as claimed in claim 8, wherein each confirmatory entry further comprises timing data.

16. The system as claimed in claim 15, wherein the timing data comprises a confirmatory time window, the confirmatory time window is within and less than or equal to a trigger time window of a trigger data set that includes the each confirmatory entry, and wherein when the time of the analysis period moves beyond a confirmatory time window of the each confirmatory entry, if a designated confirmatory ion and a corresponding designated confirmatory ion fragment of the each confirmatory entry are on the duty cycle list, the controller further removes from the duty cycle list the designated confirmatory ion and the corresponding designated confirmatory ion fragment.

17. The system as claimed in claim 15, wherein the timing data comprises a confirmatory time window delay, and wherein, when a designated trigger ion fragment is detected by the detector, the controller further adds to the duty cycle list any designated confirmatory ions and corresponding designated confirmatory ion fragments from one or more stored confirmatory data sets designated by the trigger data set of the detected designated trigger ion fragment after one or more confirmatory time window delays specified by the one or more stored confirmatory data sets.

* * * * *